US010500187B2

(12) United States Patent
Blanchard et al.

(10) Patent No.: US 10,500,187 B2
(45) Date of Patent: Dec. 10, 2019

(54) COMPOSITION COMPRISING PLANT PHENOLS FOR PREVENTING OR REDUCING TEWL AND ASSOCIATED DISORDERS AND DISEASES

(71) Applicant: NESTEC S.A., Vevey (CH)

(72) Inventors: Carine Blanchard, Le Mont-sur-lausanne (CH); Marjorie Guitard, Savigny (CH); Sebastien Holvoet, Oron-la-Ville (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 14/429,158

(22) PCT Filed: Sep. 12, 2013

(86) PCT No.: PCT/EP2013/068888
§ 371 (c)(1),
(2) Date: Mar. 18, 2015

(87) PCT Pub. No.: WO2014/044591
PCT Pub. Date: Mar. 27, 2014

(65) Prior Publication Data
US 2015/0238462 A1 Aug. 27, 2015

(30) Foreign Application Priority Data

Sep. 21, 2012 (EP) ..................................... 12185380

(51) Int. Cl.
| | | |
|---|---|---|
| *A61K 8/37* | (2006.01) | |
| *A23L 33/105* | (2016.01) | |
| *A61K 47/18* | (2017.01) | |
| *A61K 31/366* | (2006.01) | |
| *A61K 31/216* | (2006.01) | |
| *A61K 36/185* | (2006.01) | |
| *A61K 36/53* | (2006.01) | |
| *A61K 36/74* | (2006.01) | |
| *A61Q 17/00* | (2006.01) | |
| *A61Q 19/00* | (2006.01) | |
| *A23C 9/13* | (2006.01) | |
| *A23L 2/52* | (2006.01) | |
| *A61K 8/49* | (2006.01) | |

(52) U.S. Cl.
CPC .............. *A61K 31/366* (2013.01); *A23C 9/13* (2013.01); *A23L 2/52* (2013.01); *A61K 8/375* (2013.01); *A61K 8/498* (2013.01); *A61K 31/216* (2013.01); *A61K 36/185* (2013.01); *A61K 36/53* (2013.01); *A61K 36/74* (2013.01); *A61Q 17/00* (2013.01); *A61Q 19/007* (2013.01); *A23V 2002/00* (2013.01)

(58) Field of Classification Search
CPC ....... A61K 33/105; A61K 8/375; A61K 47/18
See application file for complete search history.

(56) References Cited

U.S. PATENT DOCUMENTS

2007/0293559 A1* 12/2007 Kagami ................... A23L 2/52
514/423
2010/0129324 A1* 5/2010 Crespy ................... A23L 33/14
424/93.4

FOREIGN PATENT DOCUMENTS

| DE | 10133203 | 1/2003 |
| JP | 2002293737 | 10/2002 |
| JP | 2004075619 | 3/2004 |
| WO | 2006018149 | 2/2006 |
| WO | WO 2011092581 A1 * | 8/2011 |
| WO | 2012013776 | 2/2012 |

OTHER PUBLICATIONS

Al-Sereiti MR, et al.; "Pharmacology of rosemary (*Rosmarinus officinalis* Linn.) and its therapeutic potentials"; 1999; Indian J. Expo. Biol. 1999; 37: 124-130.*
Gorska, et al.; "Identification of Lactobacillus proteins with different recognition patterns between immune rabbit sera and nonimmune mice or human sera"; 2016; BMC Microbiology; 16:17; pp. 1-11.*
Lee et al.; "Effect of rosmarinic acid on atopic dermatitis"; 2008; Journal of Dermatology; 35: 768-771.*
Healthy Skin Guide; "Olive Oil for Eczema"; https://www.healthy-skin-guide.com/olive-oil-for-eczenna.html; as evidenced by the May 5, 2011 Wayback Machine capture, https://www.healthy-skin-guide.com/olive-oil-for-eczema.html Year: 2011.*
Native Remedies®; "Skin Dr.TM"; http://www.nativeremedies.com/products/skindr-itchy-scaly-skin-scalp.html?img=458&kbid=2034, as evidenced by the Apr. 28, 2011 Wayback Machine capture, https://web.archive.org/web/20110428144614/http:// www.nativeremedies.com/products/skindr-itchy-scaly-skin-scalp.html?img=458&kbid=2034.*
Kontogianni et al.; "Phenolic compounds and antioxidant activity of olive leaf extracts"; 2012; Natural Product Research; 26(2): 186-189; Year: 2011.*
WebMD; "Eczema Health Center"; http://www.webmd.com/skin-problems-and-treatments/eczema/default.htm, as evidenced by the Jul. 2, 2011 Wayback Machine capture, https://web.archive.org/web/20110702131229/http://www.webmd.com/skin-problems-and-treatments/eczema/default.htm.*
Singh et al., "Dietary polyphenols in the prevention and treatment of allergic diseases" Clinical & Experimental Allergy, vol. 41, 2011, pp. 1346-1359.
Jang et al., "Rosmarinic Acid Attenuates 2,4-dinitrofluorobenzene-induced Atopic Dermatitis in Nc/nga Mice", International Immunopharmacology, vol. 11, Issue No. 9, Apr. 5, 2011, pp. 1271-1277, XP028265412.

* cited by examiner

*Primary Examiner* — Timothy P Thomas
(74) *Attorney, Agent, or Firm* — K&L Gates LLP

(57) ABSTRACT

Plant phenols, in particular, plant phenolic acids, like rosmarinic acid, ellagic acid, and chlorogenic acid, are used in preventing or reducing transepidermal water loss (TEWL) and associated disorders and diseases.

13 Claims, 2 Drawing Sheets

COMPOSITION COMPRISING PLANT PHENOLS FOR PREVENTING OR REDUCING TEWL AND ASSOCIATED DISORDERS AND DISEASES

CROSS REFERENCE TO RELATED APPLICATIONS

The present application is a National Stage of International Application No. PCT/EP2013/068888, filed on Sep. 12, 2013, which claims priority to European Patent Application No. 12185380.8, filed on Sep. 21, 2012, the entire contents of which are being incorporated herein by reference.

FIELD OF INVENTION

The present invention relates to the use of plant phenols for use in the treatment or prevention of a transepidermal water loss disorder (TEWL) or/and increasing skin barrier function.

BACKGROUND

The primary function of the skin is to protect the body against environmental stresses and to prevent against dehydration.

TEWL is a term used in dermatology to characterize the loss of water that passes from the inside of a body through the epidermal layer (skin) to the surrounding atmosphere via diffusion and evaporation processes.

TWEL is also the most physiological readout to assess compromised skin barrier function as it is well established that an impaired skin barrier eventually leads to loss of water throughout the skin.

Transepidermal water loss can have genetic and/or an allergic etiology.

Genetic components are involved in the water loss observed in chronological aging, atopic dermatitis, reactive skin, dry skin, atopic diathesis in rosacea and perioral dermatitis.

Allergic diseases leading to water loss include atopic dermatitis, eczema, dry skin.

In TEWL disorders, the normal water loss rate is increased due to a diminished barrier function of the epidermis. A TEWL disorder is thus characterized by the symptoms of a dehydrated epidermis like dry or scaly skin. TEWL disorders in humans are often caused or associated with atopic dermatitis (also called eczema) and reactive skin. Other diseases with skin inflammatory condition are also associated with an increased TEWL such as injury, infection and/or severe damage as in the case of burns psoriasis, and a range of inflammatory skin conditions such as atopic diathesis in rosacea and perioral dermatitis).

TEWL having a genetic component can lead to dry skin or reactive skin and TEWL having allergic component can lead to atopic dermatitis.

For the establishment of atopic dermatitis and reactive skin a genetic disposition (polymorphism genes such as in filaggrin gene or SPINK5) and an irritant like an allergen are usually required. Subjects suffering from atopic dermatitis show reactions of the skin against agents that usually do not cause any skin irritation in healthy subjects (like soap, cold, transpiration, stress).

In relation to skin barrier function, a genetic barrier function disease can lead to chronological aging, psoriasis or non allergic eczema. Allergic component of skin barrier function disease can lead to sensitive skin. Measurement of TEWL is thus a way to measure loss of water through the epidermal layer (skin) but also the skin barrier function through its TEWL component.

Previous treatments usually aimed at applying moistening skin gels or compositions comprising a variety of artificial or natural ingredients directly to the skin to treat the symptoms of TEWL (see WO 2003090670 A2).

Alternatively, a variety of nutritional supplements have been suggested (see U.S. Pat. No. 7,297,677 B2) but those did not include plant phenols. Alternative approaches aimed at avoiding those agents that caused the reaction of the skin in the environment or the diet.

It was therefore the object of the invention to provide a novel composition for the treatment of a TEWL disorder and/or to increase skin barrier function. Preferentially, this composition can also be orally administered.

SUMMARY

It is the object of the invention to provide new and alternative solutions to the problem of preventing or treating TEWL and/or increasing skin barrier function or/and for use in the prevention or treatment of atopic dermatitis or eczema. It has been surprisingly found that plant phenols are useful in preventing or treating TEWL and/or increasing skin barrier function and/or for the prevention or treatment of atopic dermatitis or eczema.

The evaluation of ingredients which are useful in the treatment or prevention of TEWL and/or skin barrier function is performed using an established mouse model atopic dermatitis (Akei et al., "Epicutaneous aeroallergen exposure induces systemic TH2 immunity that predisposes to allergic nasal responses", Journal of allergy and clinical immunology, 2005 118(1):62-69. This model induces atopic dermatitis like symptoms in mice with a decreased filaggrin expression in the skin, a rash, and erythema as well as a reduction of the TEWL. Accordingly, it is ideally suited for the testing of compounds that are candidates for the treatment or prevention of atopic dermatitis and TEWL.

Therefore, the invention relates to a composition comprising plant phenols for use in the prevention or treatment of transepidermal water loss (TEWL) disorder and/or increasing barrier function of the skin (i.e. epidermal layer) and/or for the prevention or treatment of atopic dermatitis or eczema. In a preferred embodiment, the phenols can be selected from the group consisting of rosmarinic acid, ellagic acid, punicalagins, cholorgenic acid, tannins or mixtures thereof.

The prevention or treatment of TEWL can result in an increase of skin barrier protection, can result in the prevention or treatment of atopic dermatitis, can result in the prevention or treatment of eczema, or can result in the prevention or treatment of reactive skin.

The plant phenol can be a polyphenols or a tannin. The plant phenols can be comprised in plant extracts and the composition can comprise said plant phenols. Thus, the invention also relates to a composition comprising plant extracts selected from the group consisting of extracts from thyme, pomegranate, green coffee, or mixtures thereof.

The composition can be administered orally, optionally by tube feeding. The composition can be administered to a human being or a pet animal, in particular a cat or a dog. The human being can be a young child between the age of 4 months and six years, an older child between the age of 6 to 18 years, or an adult person. Thus, the nutritional composition can be selected from the group consisting of an infant feeding composition, a follow-up formula, a growing-up milk, an infant cereal, or a baby nutritional composition. The composition can also be a nutritional composition, a pet nutritional composition, a oral nutritional supplement or a pharmaceutical product. In particular, the nutritional composition can be selected from the group consisting of a beverage product, a yoghurt product, a fermented milk, a fruit juice, or a cereal bar. The nutritional composition can be a food for specific medical purposes such as a powder to dissolve in liquid or a pills or capsules as a health care nutritional composition for oral feeding, a nutritional product for enteral feeding or a parenteral feeding product.

The composition can also be formulated for cosmetic use or can be used as a cosmetic agent. Accordingly, the composition can be in the form of an ointment, cream, milk, pomades, powder, impregnated pad, solution, gel, sprays, lotion or suspension. The composition can contain excipients which are suitable for cosmetic use.

DEFINITIONS

Figure 1A:
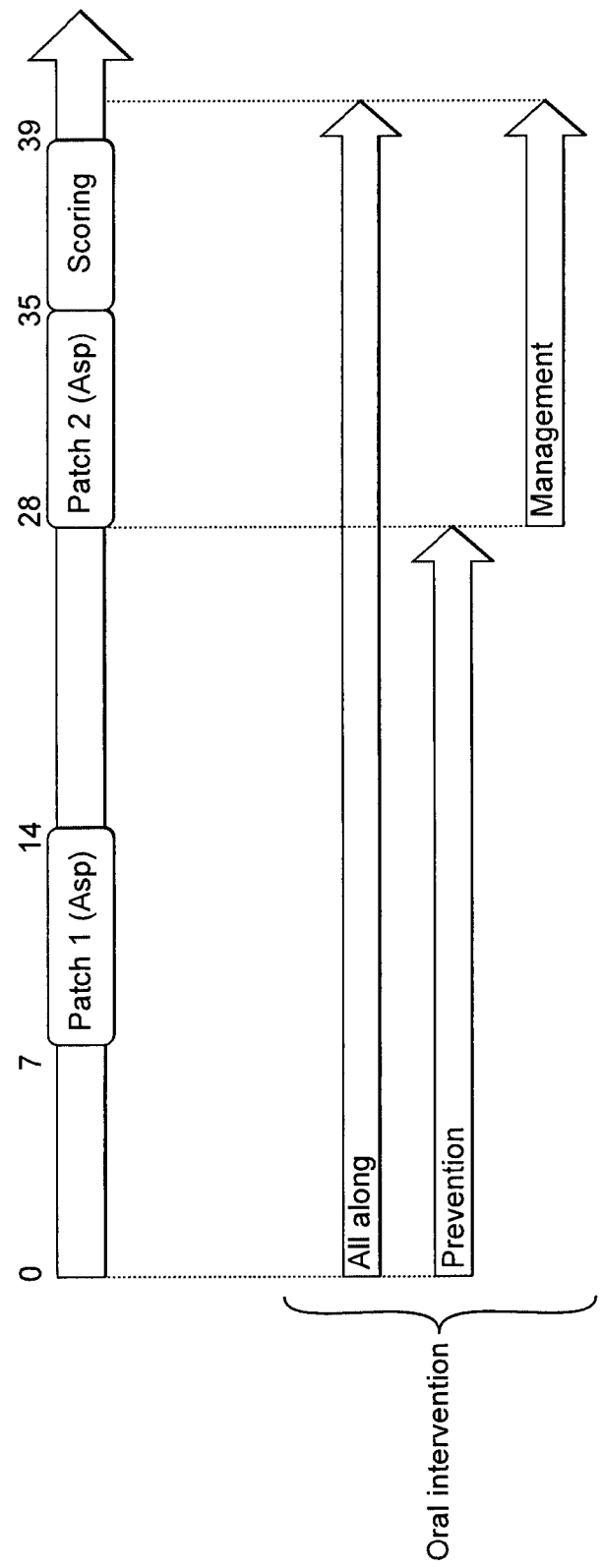
FIG. 1A. Basic experimental scheme. The scheme illustrates the model and the sequence of treatments. Two patches are applied each for 8 days with 14 days in between. The first patch effects a sensitization without visible skin symptoms. The second patch induces a variety of skin symptoms (TEWL, decreased filaggrin expression, skin alterations and inflammation etc.) "All along" means that a type of treatment was started 8 days before the first patch was applied and continued throughout all subsequent phases. "Prevention" means that a type of treatment was started 8 days before the first patch was applied and continued until the second patch was applied. "Management" means that a type of treatment was initiated concurrently with the application of the second patch and continued throughout all subsequent phases. Negative control are patches of saline, positive control is 100 µg of *Aspergiluss fumigatus* extract (GREER) for each patch.

"Transpidermal water loss (TEWL)" is defined as the measurement of the quantity of water that passes from inside a body (animal or plant) through the epidermal layer (skin) to the surrounding atmosphere via diffusion and evaporation processes. TEWL measurements are of great importance in evaluating barrier functionality of the epidermal layer. Normal rates of TEWL are compromised due to injury, infection and/or severe damage as in the case of burns. Damage to the stratum corneum and superficial skin layers not only results in physical vulnerability, but also results in an excess rate of water loss. Normal rates of TEWL are $7\pm3$ $g \cdot h^{-1} \cdot m^{-2}$. In the sense of the invention rates of TEWL above 10 $g \cdot h^{-1} \cdot m^{-2}$ are considered to be a disorder of the skin (i.e., the epidermal layer). TEWL disorders are often associated with atopic dermatitis (also called eczema or reactive skin). The etiology of these conditions is frequently associated with genetic polymorphism leading to the decreased expression of protein highly involved in the skin barrier function such as protein encoded by genes of the epidermal differentiation complex (e.g. filaggrin, involuccrin, sprr) and protein involved in tight junctions. Therefore, the invention also relates to the prevention or treatment of atopic dermatitis, eczema, or reactive skin or the symptoms of a TEWL disorder caused by atopic dermatitis, eczema, or reactive skin, burns, psoriasis, dermatitis, rosacea and idiopathic skin inflammation, dry skin. Symptoms of TEWL are, in particular, a dry or scaly skin.

"Plant phenols" are a class of natural organic compounds. They comprise one or more phenolic groups. Only phenols that occur in plants and artificially synthesized phenols that are identical to phenols naturally occurring in plants are considered here.

"Phenolic groups" are groups that comprise a phenyl group bonded to a hydroxyl group. The hydrogen of the ring carbons of the phenolic groups can be substituted with further residues (like hydroxyl-, alkan-, alken-residues, ring C formed as carboxyl etc.). A particular preferred substitution is a further hydroxyl group.

"Plant polyphenols" in the sense of the invention are phenols comprising more than 2 phenolic groups.

For the purposes of this invention, the terms "treating" or "treatment" mean to decrease or alleviate the symptoms suffered by an animal especially the symptoms of a skin disorder and/or assist in the management of a skin disorder. The terms "treatment" and "treating" further mean to promote or aid recovery of the skin for example to improve the appearance and condition of the skin. The terms "prevention" or "preventing" mean to stop the onset of symptoms or to reduce the severity of such symptoms suffered by an animal. In addition the terms "prevention" or "preventing" mean to delay the onset of symptoms.

"Atopic dermatitis" (AD, also called eczema or reactive skin) is an inflammatory, chronically relapsing, non-contagious and pruritic (itch causing) skin disorder. The skin of a patient with atopic dermatitis overreacts and easily to irritants, food, and environmental allergens and becomes red, flaky and very itchy (becomes a reactive skin). It also becomes vulnerable to surface infections caused by bacteria. The skin on the flexural surfaces of the joints is often affected in human subjects. Symptoms may vary from person to person but they are usually present as a red, inflamed, and itchy rash and can quickly develop into raised and painful bumps. The skin tends to be more sensitive and may thicken, crack, become dry or scale. Epidermal barrier dysfunction is considered to be an explanation on the physiopathology of atopic dermatitis. Changes in certain genes encoding structural proteins, epidermal proteases and protease inhibitors predispose to a defective epidermal barrier and increase the risk of developing atopic dermatitis. The strong association between both genetic barrier defects and environmental insults to the barrier with atopic dermatitis suggests that epidermal barrier dysfunction is a primary event in the development of this disease. Without being bound to any theory we believe that increasing barrier function can effect a treatment of atopic dermatitis. An important indicator of barrier function is TEWL. It is assumed that TEWL can be reduced by the administration of plant phenols and thereby atopic dermatitis can be treated. The effect may be mediated by improving the tight junction system of the skin.

"Barrier function" is the function of the (epidermal) barrier to prevent the transition of agents, allergens, microorganisms, or water through the epidermal layer. Increasing the barrier function thus means that the barrier function of the skin is strengthened. Thereby the transition of agents, allergens, microorganisms, or water through the epidermal layer is decreased. In particular, this increase of barrier function may be mediated by a reduction of the interstitial room between the epidermal cell layers. This may be effected by increasing the number of tight junctions or/and increasing the quality of the tight junctions between the epidermal cells and/or increased expression of protein of the epidermal differentiation complex (such as filaggrin, sprr, NICE, involucrin, loricrin).

DETAILED DESCRIPTION OF THE INVENTION

The section headings serve to clarify the subject matter and should not be interpreted to limit the subject matter. If ranges of values are disclosed each individual value is considered to be covered by the range, in particular, each integer number. If not noted otherwise, values in % relate to weight/weight (w/w) values.

It has been surprisingly found that certain plant phenols are useful for decreasing TEWL and/or for increasing skin barrier protection or/and for use in the prevention or treatment of atopic dermatitis or eczema. This finding was made in a mice model for atopic dermatitis that allowed determining TEWL. Therefore, it can be concluded that plant phenols can be used in the treatment or prevention of TEWL disorders, atopic dermatitis or, in general, for increasing barrier function. Without wanting to be bound to any theory it is believed that plant phenols increase epidermal barrier function by increasing the number or quality of tight junctions in the epidermal cell layer.

Compositions

The compositions of the invention can comprise several ingredients, the main active ingredient being plant phenols, which are explained in more detail below.

Plant Phenols

The composition comprises at least one plant phenol. Plant phenols comprise at least 1, 2, 3, 4, 5, or 6 phenolic residues. Plant phenols can comprise 1 to 6, 1 to 5, 1 to 4, 1 to 3, or 1 to 2 phenolic residues. Particularly preferred are plant phenols comprising 1 or 2 phenolic residues. Particularly preferred are plant polyphenols.

The plant phenols preferentially do merely consist of hydrogen, carbon, and oxygen. The plant phenols preferentially do comprise or consist of a residue selected from the group consisting of at least one cyclohexan residue, phenolic residue, H— residue, OH— residue, C= residue, $CO_2H$— residue, ethyl residue, —O— residue.

The composition can comprise at least one, at least two, at least three, or at least four different plant phenols. It can be expected that a combination of plant phenols will show synergist effects on TEWL. The phenols are phenols that occur in natural plant sources. The natural sources can be thyme, pomegranate, or green coffee, or mixtures thereof. The phenols may be extracted from natural plant sources by any known extraction technique, like an extraction with water or an organic solvent, like ethanol or ether.

The composition can comprise a plant extract comprising the plant phenols. The composition can comprise plant extracts selected from the group consisting of thyme, pomegranate, green coffee, or any possible combination or mixture thereof. In particular, the composition can comprise thyme, pomegranate and green coffee extract.

The plant extract can be thyme extract and comprise rosmarinic acid.

The plant extract can be pomegranate extract and comprise ellagic acid.

The plant extract can be green coffee and comprise cholorgenic acid.

The composition can comprise 1 to 7%, 2 to 6%, 3 to 5 or 4% of a plant extract, in particular, a thyme extract. The plant extract, in particular, the thyme extract can comprise 4 to 8%, 5 to 7%, or 6% of a plant phenol, in particular, rosmarinic acid.

The plant extract can comprise 20 to 70%, 25 to 60%, 30 to 55%, 35 to 50%, 35 to 45%, or 40 to 50% of plant phenols, in particular, a pomegranate or green coffee extract. The composition, can comprise 0.25 to 2%, 0.5 to 1.5%, 0.75 to 1.25%, or 1% of a plant extract, in particular, a pomegranate or green coffee extract.

The plant phenols can be phenolic acids. In particular, the plant phenols can be rosmarinic acid, methylated rosmarinic acid, coumaric acid, ferulic acid; ellagic acid, ellagitannins, punicalagins, gallic acid, gallotannin; cinnamic acids (like caffeic acid, ferulic acid and p-coumaric acid) and esthers of cinnamic acid with (−)-quinic acid, one preferred cinnamic acid esther is cholorgenic acid, derivates of cholorgenic acid like its 3-O-glucoside, 3-O-galactoside and 3-O-arabinoside are also considered. Phenols can also be flavonoids or catechins. The respective plant phenols are structurally related and it can be therefore expected that they have a similar effect on TEWL. It is also contemplated that any of the above described plant phenols can be excluded from the composition if this deems to be appropriate. In a particular embodiment epicatechin, catechin, flavonoids, or/and lignin are excluded from the composition. Mixtures of these plant phenols are also contemplated. In particular, the mixture can comprise at least 1, 2, 3, 4, 5, 6, 7, 8, 9, 10, 11, 12 of the above described plant phenols. The mixture can comprise at least 1-6, 1-5, 2-4, or of the above described plant phenols. The composition can comprise any permutation of the above described phenols in the composition.

Each of the phenols or the sum of a combination of those phenols can be present in the composition at a concentration of between 0.1% and 1%, between 0.15% and 0.8%, between 0.15% and 0.7%, between 0.15% and 0.6%, between 0.15% and 0.5%, between 0.2% and 0.5%, between 0.25 and 0.5% or be present at a concentration of 0.3%, 0.4%, or 0.45%.

Particularly preferred phenols are rosmarinic acid, ellagic acid, and cholorgenic acid, or any possible combination or mixture thereof.

Formulations

The above described compositions can be formulated in liquid or solid form. The compositions can further comprise at least one additional active agent, carrier, vehicle, excipient, or auxiliary agent identifiable by a person skilled in the art upon reading of the present disclosure.

The composition can be in the form of a nutritional composition, oral nutritional supplement or pharmaceutical product. A nutritional composition, nutritional supplement or pharmaceutical product can comprise the composition or kit of the invention.

Nutritional Composition

As used herein, the term "nutritional composition" includes, but is not limited to, complete nutritional compositions, partial or incomplete nutritional compositions, and disease or condition specific nutritional compositions. A complete nutritional composition (i.e., those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as a nutritional supplement. An oral supplemental nutritional composition contains mainly or exclusively the essential active ingredients of the claimed composition (the plant phenols) and can be consumed in addition to the regular nutrition of a patient.

A disease or condition specific nutritional composition is a composition that delivers nutrients or pharmaceuticals and can be a complete or partial nutritional composition. A nutritional composition may additional comprise the following nutrients and micronutrients: a source of proteins, a source of lipids, a source of carbohydrates, vitamins and minerals. The composition may also contain anti-oxidants, stabilizers (when provided in solid form) or emulgators (when provided in liquid form). In a preferred embodiment the composition is amino acid-based formula, that means, the only source of amino acids are free amino acids.

Thus, in another embodiment, the nutritional composition further includes one or more amino acids. Non-limiting examples of amino acids include Alanine, Arginine, Asparagine, Aspartate, Citrulline, Cysteine, Glutamate, Glutamine, Glycine, Histidine, Hydroxyproline, Hydroxyserine, Hydroxytyrosine, Hydroxylysine, Isoleucine, Leucine, Lysine, Methionine, Phenylalanine, Proline, Serine, Taurine, Threonine, Tryptophan, Tyrosine, Valine, HICA (Alpha-Hydroxyisocaproic Acid), HIVA (Alpha-Hydroxyisovaleric Acid), HIMVA (alpha-hydroxymethylvaleric acid) or a combination thereof. In a preferred embodiment, non-limiting examples of amino acids include proline, hydroxyproline, hydroxytyrosine, hydroxylysine and hydroxyserine and combinations thereof.

In a further embodiment the nutritional composition may comprise minerals such as sodium, potassium, calcium, phosphorus, magnesium, chloride, iron, zinc, copper, manganese, fluoride, chromium, molybdenum, selenium, iodine or any combination thereof.

In a further embodiment the nutritional composition comprises further vitamins such as Vitamin A, Vitamin E, Vitamin C, Vitamin B1, Vitamin B2, pantothenic Acid, Vitamin B6, Vitamin B12, Niacin, Folic Acid, Biotin and Choline or any combination thereof.

In one embodiment, the nutritional composition is selected from the group consisting of an infant feeding composition, a follow-up formula, a growing-up milk, an infant cereal, or a baby nutritional composition. These products are particularly well suited to address and solve the problem of the prevention or reduction of symptoms of TEWL in babies and young children. However, other products like beverages and powders can also be chosen for older children and adults as described in the following.

In a further embodiment, the nutritional composition is selected from the group consisting of a beverage product, a yoghurt product, fermented milk, a fruit juice, or a cereal bar. These nutritional compositions are well suited for administering plant phenols to older children and adult humans. The nutritional compositions can well be enriched with plant phenols and have a credible image to provide a health oriented functional nutritional composition to the consumers.

In a still further embodiment, the nutritional composition is a food for specific medical purposes such as a health care nutritional composition for oral feeding, and/or a nutritional product for enteral or parental feeding. In the latter case it will only include ingredients which are suitable for parenteral feeding. Ingredients that are suitable for parental feeding are known to the person skilled in the art. In particular, a parental feeding composition will contain the plant phenols in pure or substantially pure form (i.e. usually not be provided in the form of plant extracts which are only enriched for the plant phenol) but the composition can also comprise other ingredients that are known to be suitable for parenteral nutrition. A further advantage of the invention is that plant phenol can be provided in relatively high local concentration and low volumes of a medical nutritional composition and hence be administered effectively to patients in such need.

Cosmetical Use of the Composition

The composition can also be used for cosmetic applications. A cosmetic treatment may differ from a therapeutical treatment by lacking the characteristics of a therapeutical treatment like for example the involvement of a medical practitioner. In a particular embodiment relating to the cosmetical use the composition can be applied topically, in particular, to the skin. By the topical route, the cosmetical compositions based on compounds according to the invention are preferably intended for the treatment of the skin and of the mucous membranes and may be provided in the form of ointments, creams, milks, pomades, powders, impregnated pads, solutions, gels, sprays, lotions or suspensions. They may also be provided in the form of microspheres or nanospheres or lipid or polymeric vesicles or polymeric patches or hydrogels allowing controlled release. These compositions for topical administration may be provided either in anhydrous form or in aqueous form depending on the clinical indication.

The pH of the composition can be normally of the order of 6.5 to 8 and preferably in the range from 6.5 to 7.5. Since the plant phenols are the active ingredient, the composition intended for cosmetic or topical use normally contains a carrier, an excipient or a vehicle compatible with the method of administration selected. For example, for preparing creams and similar products, a paste-like, semi-fluid or fluid ointment base is used which, of course, is non-toxic to the body and which is capable of being emulsified with the plant phenols (oil-in-water and water-in-oil emulsion). Examples of ingredients for the base include cetyl alcohol, lanolin, petroleum jelly, liquid paraffin and polyoxyethylene sorbitan esters such as the palmitates, oleates and stearates, and these substances, may all be used either separately or in any combination for preparing the base. This base preferably also contains triglycerides containing essential fatty acids and, optionally, a high proportion of liposoluble vitamins, long-chain fatty alcohols, esters of branched-chain fatty acids and emulsive monoglycerides. Formulations intended for application to base skin desirably have a chemical composition as close as possible to that of human sebum. In certain cases, one or more emulsifiers and/or surfactants may be incorporated in the composition, depending on the type of formulation required.

Finally, the composition generally contains antioxidants, bactericidal and fungicidal agents and, if desired, colorants, pigments and/or perfumes.

The composition according to the invention may also be presented in the form of aqueous dispersions (lotions such as, for example, pre-shave or after-shave lotions), liquid emulsions (body milks, cleansing milks), viscous emulsions (masks), aqueous or anhydrous gels. The composition according to the invention may also be incorporated in make-up foundations and hair care products.

The composition is packaged according to the use and nature of the product. Creams, ointments, etc. are generally filled in jars or tubes whereas lotions, milks or similar products are more frequently packed in bottles or containers capable of dispensing the composition in the form of an aerosol or foam.

The composition according to the invention may be used as a topical cosmetic, for example in the form of a cream or milk, and has a softening, soothing and revitalising effect. It may also be used for preventing inflammation, particularly of the nappy rash type, in babies and for treating the breasts and nipples of nursing mothers.

The composition also has a curative use and may be prescribed for the following therapeutic applications: atopic dermatitis (also called eczema), reactive skin, injury, infection and/or severe damage of the skin as in the case of burns, psoriasis, and a range of inflammatory skin condition such as atopic diathesis in rosacea and perioral dermatitis.

A normal TEWL in human (e.g. forearm) and animal is $7\pm3$ $g \cdot h^{-1} \cdot m^{-2}$, an abnormal TEWL is defined as above 10 $g \cdot h^{-1} \cdot m^{-2}$. Thus, reducing TEWL to a level that is closer to $7\pm3$ $g \cdot h^{-1} \cdot m^{-2}$ than a previous TEWL level that was greater than 10 $g \cdot h^{-1} \cdot m^{-2}$ (e.g. 10.5, 11.0, 12.0, 13.0, 14.0, 15.0, 20.0, 25.0) is considered to relate to a cosmetic treatment of a TEWL disorder. In particular, the reduction of a previous TEWL level that was greater than 10 $g \cdot h^{-1} \cdot m^{-2}$ a by 0.5, 1.0, 1.5, 2.0, 3.0, 4.0, 5.0 or 10.0 to a value that is closer to or in the range of $7\pm3$ $g \cdot h^{-1} \cdot m^{-2}$ is considered to relate a cosmetic treatment of TEWL.

Kits

The above compositions may also be provided as kits. In those kits the all or a part of the ingredients of the above described compositions are provided in a separate (i.e. not mixed) form. A kit of the invention can comprise the plant phenols on the one hand and any other ingredients on the other hand in separate form. A kit of the invention can comprise at least two or three plant phenols provided in a separate form. In an alternative embodiment, the kits can comprise each of the ingredients of the above described composition in a separate form.

Therapeutical/Cosmetical Uses and Methods

The composition or the kit of the invention can be used in the therapeutical or cosmetical treatment or prevention of TEWL, or the treatment of prevention of a skin disorder characterized by a TEWL which is increased compared to a subject not suffering from the disorder. The composition or the kit of the invention can be used in the treatment or prevention of atopic dermatitis (eczema or reactive skin) or for increasing skin barrier function (i.e. epidermal barrier function). The composition or the kit can effect a reduction of TEWL. The composition or the kit can effect a reduction of TEWL to a TEWL value that is substantially identically to the TEWL of a subject not suffering from the disorder. The composition or the kit can effect a reduction of TEWL to a TEWL value that is closer to the TEWL value of a subject not suffering from the disorder.

A normal TEWL in human (e.g. forearm) and animal is $7\pm3$ $g \cdot h^{-1} \cdot m^{-2}$, an abnormal TEWL is defined as above 10 $g \cdot h^{-1} \cdot m^{-2}$. Thus, reducing TEWL to a level that is closer to $7\pm3$ $g \cdot h^{-1} \cdot in^{-2}$ than a previous TEWL level that was greater than 10 $g \cdot h^{-1} \cdot m^{-2}$ (e.g. 10.5, 11, 12, 13, 14, 15, 20, 25) is considered to relate to a treatment of a TEWL disorder. In particular, the reduction of a previous TEWL level that was greater than 10 $g \cdot h^{-1} \cdot m^{-2}$ a by 0.5, 1.0, 1.5, 2.0, 3.0, 4.0, 5.0 or 10.0 to a value that is closer to or in the range of $7\pm3$ $g \cdot h^{-1} \cdot m^{-2}$ is considered to relate a treatment of TEWL.

The composition or the kit of the invention can also be used in a method for the cosmetical or therapeutical treatment or prevention of TEWL, or the cosmetical or therapeutical treatment of prevention of a skin disorder characterized by a TEWL which is increased compared to a subject not suffering from the disorder.

The compositions and kits can be provided in a form that is suitable for oral or topical administration and then be administered accordingly. Oral administration is preferred. Administration can start before the symptoms of a TEWL disorder occur in a subject, concurrently together with the appearance of the symptoms or after the symptoms have shown. Administration can be performed for 1, 20, 30, 60, 120, 360 days or longer. If the subject is a human, the subject to which the composition is administered, can be between the age of 4 months and 6 years, between the age of 6 years and 18 years, or be an adult person.

In an embodiment, the composition is intended for consumption by an animal, preferably a cat or a dog. Similarly as with humans, allergies and symptoms of such allergies can be observed with animals, in particular with domesticated animals and animals kept as pets. Advantageously, the current invention provides a liquid which can be provided to a companion animal by his owner.

The sum of plant phenols in the composition is administered to a human being in an amount in the range from 25 mg to 10 g per day, from 50 mg to 10 g per day, preferably from 100 mg to 5 g per day, even more preferably from 300 mg to 1 g per day. These preferred doses allow to provide on one hand sufficient plant phenols to a relevant patient per day in order to provide the expected health benefit and on the other hand not to overdose plant phenols to prevent the risk of any potential undesirable or toxic effects to the patient.

Methods of Production

A method for producing the above described composition is provided and comprises providing at least one of the above described plant phenols, adding optionally at least one further ingredient selected from the group consisting of fat, protein, carbohydrate or therapeutic/cosmetic excipient, adding optionally at least one nutrient or micronutrient, adding a carrier or/and water.

Those skilled in the art will understand that they can freely combine all features of the present invention disclosed herein. In particular, features described for different embodiments of the present invention may be combined. Further advantages and features of the present invention are apparent from the figures and examples.

EXAMPLES

Example 1

Establishment of a Mice Model for Atopic Dermatitis and "Management" with Orally Administered Plant Phenols FIG. 1A illustrates the basic experimental scheme. The scheme illustrates the model and the sequence of treatments. 5-8 weeks old female Balb/c mice were sensitized by epicutaneous application of 100 µg of an allergic extract. A small part of the back of the mouse was shaved. A patch of sterile gauze (1×1 cm) with the allergen was secured to the skin with a bio-occlusive transparent dressing 2461 (Johnson and Johnson) and a Band-Aid. The patch remained on the skin for sensitization periods of 4 to 8 consecutive days till it felt or was removed at day 8 (Patch 1). 14 days after the last sensitization day the procedure was repeated with a second patch (Patch 2) which again remained on the skin for 4-8 days.

The first patch effects a sensitization without visible skin symptoms. The second patch induces a variety of skin symptoms, like an increase of TEWL, a decreased filaggrin expression (due to Th2 cytokine (IL-4, IL-13 expression)), an increased skin score indicated by erythema, excoriation, lichenfication, baldness, dryness), an increased skin thickness at the patch site and indications of inflammation of the skin at the patch site (increased collagen deposition and inflammatory cell infiltration) skin alterations and inflammation etc.)

In FIG. 1A "all along" means that a type of treatment was started 8 days before the first patch was applied and continued throughout all subsequent phases. "Prevention" means that a type of treatment was started 8 days before the first patch was applied and continued until the second patch was applied. "Management" means that a type of treatment was initiated concurrently with the application of the second patch and continued throughout all subsequent phases. Negative control are patches of saline, positive control is 100 μg of *Aspergilus fumigatus* extract.

|  | (n=) | Epicutaneous sensitization | Challenges | Management |
|---|---|---|---|---|
| Group A | 8 | 2X saline | 2x ASP | none |
| Group B | 8 | 2X ASP | 2x ASP | none |
| Group C | 8 | 2X ASP | 2x ASP | Thyme |
| Group D | 8 | 2X ASP | 2X ASP | Pomegranate |
| Group E | 8 | 2X ASP | 2X ASP | Green Coffee |

In a "management" experiment thyme extract, pomegrenate extract or green coffee was administered for 12 days concomitante to the second patch (see FIG. 1). The standard diet was a normal commercial diet from KLIBA. The experimental diets contained additionally 6% thyme (containing 5% rosmarinic acid), 1% pomegranate (containing 40% ellagic acid), or 1% green coffee (containing 40% rosmarinic acid). The diet and water were provided ad libitum. Based on the consumption of the diet by the mice it can be determined that the mice consumed about 16 g/100 g body weight of chow containing or not the extract, so approximatively 4 gram of chow per mouse (25 g of body mass) and per day. This corresponds to approximately 10-20 mg of plant phenols per day. In the negative control the second patch did only contain saline and not contain any *Aspergillus* extract while the positive control contained 100 μg of *Aspergillus* extract. Both the mice of the negative and the positive control received the standard diet without plant phenols. Eight mice were used in every experimental group. The water loss was determined in comparison to the negative control (saline). Scoring was performed 1, 2, 3 and 4 days after removal of the second patch. Bars represent median and interquartile ranges. Water loss is determined by the TEWLmeter method and given in $g \cdot h^{-1} \cdot m^{-2}$.

Figure 1B:
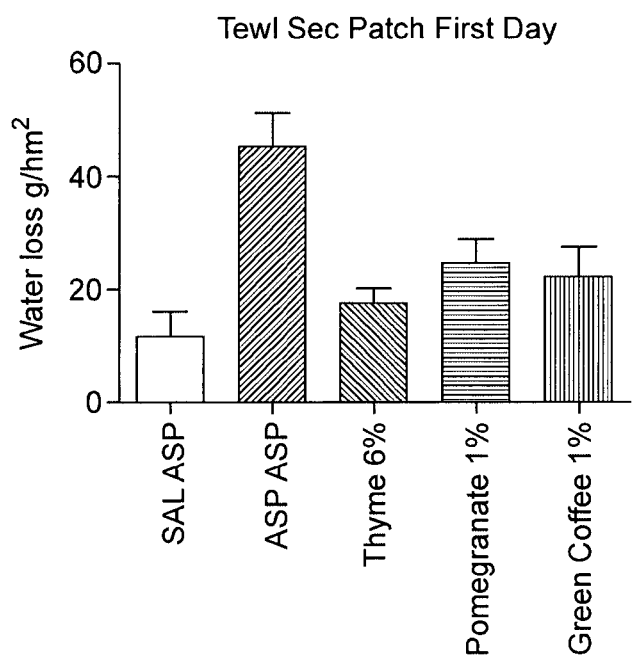
FIG. 1B. "Management" with orally administered plant phenols. In a "management" experiment thyme extract, pomegrenate extract or green coffee were administered for 2 weeks.
Figure 1C:
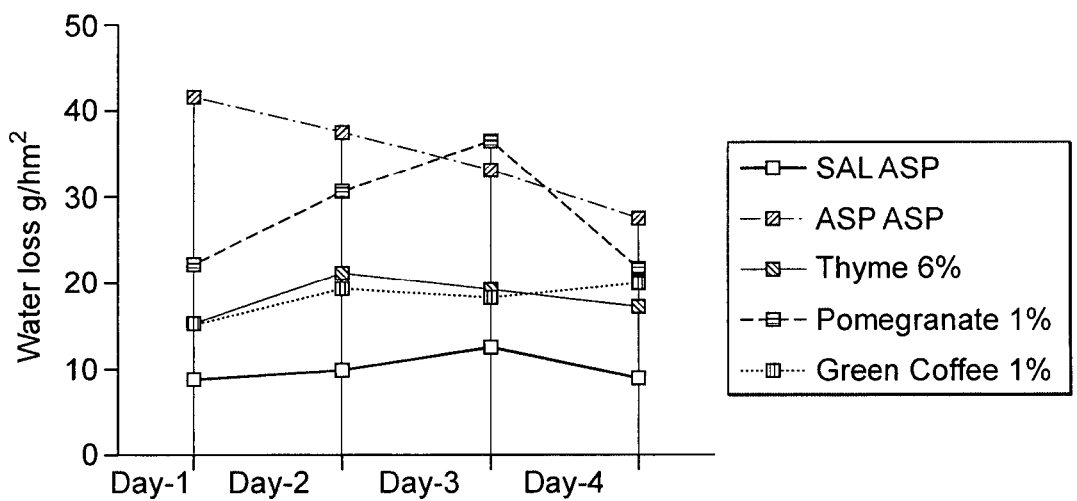
FIG. 1C. "Management" measured over the course of 4 days after the removal of the second patch. Continuation of experimental setting explained with respect to FIG. 2. Only the average values of TWEL are provided.

As can be seen in FIGS. 1B & 1C all phenol extracts substantially mitigated the effect of the *Aspergillus* extract on TEWL.

FIG. 1C provides further data points regarding the above described management experiment. The effect on TEWL was measured over the course of 4 days after the removal of the second patch. As can be seen in FIG. 1A the mitigating effect of all tested plant phenols was observed over almost the entire observation period while an effect of pomegranate extract on TEWL could not be observed on day 3. However, day 4 again showed the effect observed with the other extracts. While Green coffee and thyme extracts inhibit the increased TEWL, the pomegranate extract delayed apparition of the increased TEWL suggesting different mechanism of action on the improvement of the skin barrier function (increased of tight junction, decrease of inflammation and/or up regulation of protein or factors involved in the skin barrier function). Therefore, it can be concluded that plant phenols reduce TEWL induced by *Aspergillus* extract.

Example 2

Clinical Trial

Seven cohorts of 20-30 people in the age of 18-60 suffering from TEWL caused by reactive skin and or atopic dermatitis receive the compositions indicated in the following table. A smaller number of cohorts can also be chosen when only a smaller number of compositions is to be tested.

The thyme extracts contains 5% of the plant phenol rosmarinic acid, the pomegranate extract contains 40% of the plant phenol ellagic acid and 1% the green coffee 45% of the plant phenol cholorgenic acid (Monteloeder, Spain).

|  | Number of subjects | Agent(s) |
|---|---|---|
| Group A | 15 | Water |
| Group B | 15 | 6% thyme extract |
| Group C | 15 | 1% Pomegranate extract |
| Group D | 15 | 1% Green coffee extract |
| Group E | 15 | 2.5% Thyme extract, 0.5% Pomegranate extract |
|  | 15 | 2% Thyme extract, 0.4% Pomegranate extract, 0.45% green coffee extract |

The subjects receive the extracts in such an amount that 500 mg of the respective plant phenol(s) are administered daily. The TEWL is determined by the TEWLMeter apparatus at day 15 and 30 after start of the study. Known associated symptoms like the SCORAD (SCOre for Atopic Dermatitis), the number or severity of erythema, the number or severity of excoriations, the number or severity of lichenifications, and the severity of dryness of the skin are also observed in the study.

The invention claimed is:

1. A method for treatment of a transepidermal water loss (TEWL) disorder and/or increasing skin hydration in an individual in need thereof, the method comprising orally administering to the individual a composition consisting of (i) plant phenols, (ii) an amino acid selected from the group consisting of hydroxylysine, hydroxyserine and combinations thereof, (iii) a source of lipids, (iv) a source of carbohydrates, (v) optionally a vitamin, (vi) optionally a mineral, (vii) optionally an anti-oxidant, and (viii) optionally a component selected from the group consisting of stabilizers and emulgators.

2. The method according to claim 1 wherein the individual has atopic dermatitis, dry or reactive skin, eczema, or skin dehydration.

3. The method of claim 1 wherein the plant phenols are selected from the group consisting of rosmarinic acid, ellagic acid, cholorgenic acid, and mixtures thereof.

4. The method according to claim 1 wherein the individual has atopic dermatitis or eczema.

5. The method of claim 1 wherein the individual is a human or a pet.

6. The method of claim 1 wherein the individual is selected from the group consisting of a young child between the age of 1 month and six years, an older child between the age of 6 to 18 years, and an adult.

7. The method of claim 1 wherein the composition is administered to the individual in a dose comprising 300 mg to 1 g of the plant phenols/kg of body weight per day.

8. The method of claim 1, wherein the composition is administered to the individual in a dose ranging from 25 mg to 10 g of the plant phenols per day.

9. The method of claim 1 wherein a vitamin is present and is selected from the group consisting of Vitamin A, Vitamin E, Vitamin C, Vitamin Bi, Vitamin B2, Pantothenic Acid, Vitamin B6, Vitamin B12, Niacin, Folic Acid, Biotin, Choline, and combinations thereof.

10. The method of claim 1 wherein the composition is administered to the individual for at least 120 days.

11. The method of claim 1 wherein the plant phenols are rosmarinic acid.

12. The method of claim 1, wherein the composition is an oral nutritional supplement.

13. A method for treatment of a transepidermal water loss (TEWL) disorder and/or increasing skin hydration, in an individual in need thereof, the method comprising orally administering to the individual a composition comprising plant phenols and an amino acid selected from the group consisting of hydroxylysine, hydroxyserine and combinations thereof.

* * * * *